United States Patent [19]

Daniele et al.

[11] Patent Number: 5,704,469
[45] Date of Patent: Jan. 6, 1998

[54] SUTURE TRAY PACKAGE HAVING GROOVED WINDING SURFACE

[75] Inventors: Robert A. Daniele, Flemington; Anthony Esteves, Somerville; Martin Sobel, Flemington, all of N.J.; Robert J. Cerwin, Pipersville, Pa.; Marvin Alpern, Glen Ridge; Joseph Stanley Siernos, Whitehouse Station, both of N.J.

[73] Assignee: Ethicon, Inc., Somerville, N.J.

[21] Appl. No.: 723,736

[22] Filed: Sep. 30, 1996

Related U.S. Application Data

[62] Division of Ser. No. 494,647, Jun. 23, 1995, Pat. No. 5,628,395.
[51] Int. Cl.$^6$ .................................. A61B 17/06
[52] U.S. Cl. .................. 206/63.3; 206/339; 206/380
[58] Field of Search ...................... 206/63.3, 227, 206/339, 380, 382, 383; 606/228

[56] References Cited

U.S. PATENT DOCUMENTS

| | | |
|---|---|---|
| 3,338,401 | 8/1967 | Regen, Jr. .................. 206/63.3 |
| 3,972,418 | 8/1976 | Schuler et al. .............. 206/63.3 |
| 4,961,498 | 10/1990 | Kalinski et al. ............. 206/339 |
| 4,967,902 | 11/1990 | Sobel et al. ................ 206/63.3 |
| 5,052,551 | 10/1991 | Cerwin et al. .............. 206/63.3 |
| 5,056,658 | 10/1991 | Sobel et al. ................ 206/63.3 |
| 5,213,210 | 5/1993 | Cascio et al. ............ 206/63.3 X |
| 5,222,978 | 6/1993 | Kaplan et al. ................ 606/228 |
| 5,246,104 | 9/1993 | Brown et al. .............. 206/63.3 |
| 5,462,162 | 10/1995 | Kaplan et al. ................ 206/339 |
| 5,468,252 | 11/1995 | Kaplan et al. ................ 606/228 |

*Primary Examiner*—Bryon P. Gehman
*Attorney, Agent, or Firm*—Emil Richard Skula

[57] ABSTRACT

A suture package having a base member, an upwardly extending outer wall about the periphery of the base member, a plurality of grooves in the base member for receiving a suture, and a top lid member. The package has a central needle park and a discharge opening in the lid member for removing a needle and suture from the package. The package may alternatively have spoke members and rib members extending up from the base member containing grooves which form a suture channel for receiving a suture.

11 Claims, 7 Drawing Sheets

SUTURE TRAY PACKAGE HAVING GROOVED WINDING SURFACE

This is a division of application Ser. No. 08/494,647, filed Jun. 23, 1995, now U.S. Pat. No. 5,625,393, which is hereby incorporated by reference.

TECHNICAL FIELD

The field of art to which this invention relates is packaging, in particular, packages for surgical needles and sutures.

BACKGROUND OF THE INVENTION

Packages for surgical needles and sutures are well known in the art. Conventional packages may consist of foldable cardboard or paper having a plurality of foldably connected panels for receiving sutures. Such packages typically have needle parks for mounting needles. The packages are designed to protect the needles and sutures during sterilization, shipping and handling. The packages are further designed to provide ease of removal of the needles and sutures. Conventional plastic packages are also available for surgical needles and sutures. The plastic packages typically have an oval shape or circular shape with a peripheral suture channel for containing one or more sutures. A needle park is typically positioned interior to the channel for mounting surgical needles. The plastic packages are believed to have several advantages over paper packages in that they are easy to load, tend to maintain the suture in a controlled position within the channel, and provide ease of dispensing. Suture packages having channels for containing sutures are disclosed in the following U.S. patents which are incorporated herein by reference: U.S. Pat. No. 4,967,902; U.S. Pat. No. 5,052,551; U.S. Pat. No. 4,967,902; U.S. Pat. No. 5,131,533; U.S. Pat. No. 5,213,210; U.S. Pat. No. 4,961,498.

Although the packages of the prior art are known to function appropriately in containing surgical sutures and needles, there is a constant need in this art for improved suture packages. In particular, there is a need for a suture package having a suture channel which can be readily utilized in automated suture winding apparatuses. There is a further need in this art for a suture package having a suture channel which has the capability of reducing the incidence of suture "lock-ups" when sutures are withdrawn from the package, and which will retain sutures in an "arranged wind" pattern.

DISCLOSURE OF THE INVENTION

Therefore, it is an object of the present invention to provide an improved suture package having a winding channel which is easy to use in an automated suture winding process.

It is a further object of the present invention to provide a suture package having a winding channel which decreases the incidence of suture "lock-ups" when sutures are withdrawn from the package.

It is a further object of the present invention to provide a suture package which maintains sutures in an "arranged wind" pattern during shipping and handling.

Accordingly, a package for a surgical needles and suture is disclosed. The package has a flat base member having an outer periphery, a top and a bottom. First and second hub members extend from the top of the base member. An outer wall extending from the base member is located about the periphery of the base member. The outer wall has an inner surface, an outer surface and a top. A plurality of suture spoke members extend from top of the base member. Each spoke member has a top and sides. The suture spoke members connect each hub with the outer wall. At least one rib member extends from the base member. Each rib member has a top and sides. Each rib member connects opposed sections of the outer wall. There are a plurality of grooves extending into the tops of each spoke member and each rib member. The grooves form a suture channel for receiving and retaining a suture. The grooves have an opening, a bottom and sides. A needle park for retaining a surgical needle is positioned on top of the base member, preferably formed from an opening in a section of one or more rib members forms the needle park. A flat lid member having a periphery is mounted to the top of the outer wall. The flat lid member has a top, a bottom, a suture exit opening and an outer periphery. In a preferred embodiment, a closure lip for securing the lid to the top of the outer wall extends from the outer surface of the outer wall. The lip is bent over or staked to secure the lid to the top of the outer wall. The term "to stake" is a commonly used term in this art and is defined to mean crushing or otherwise deforming a member to mechanically secure a lid or other package component in place.

Yet another aspect of the present invention is a suture package. The suture package has a substantially flat base member. The base member has a top, a bottom, and an outer periphery. An outer wall extends upwardly from the top of the base member about its outer periphery. The outer wall has a top, an inner side, and an outer side. A plurality of suture receiving grooves is contained in the top of the base member. The grooves are preferably concentric, although a single continuous groove may be used, e.g., in the form of a spiral. The grooves have an opening, a bottom and sides. A needle park is positioned on the top side of the flat base member interior to the grooves. A flat, lid member is mounted in the package. The flat, lid member has a top, a bottom, a suture exit opening and an outer periphery. In a preferred embodiment, a closure lip for securing the lid to the top of the outer wall extends from the outer surface of the outer wall.

A needle and suture combination is removed from the packages of the present invention by initially removing the needle from the needle park and pulling the needle and suture through the exit opening in the lid member. Suture coils preferably are withdrawn successively out from the grooves and between the bottom of the lid member and the top of the rib members, spoke members or base member, and then through the exit opening in the lid member.

The foregoing and other features and advantages of the present invention will become more apparent from the following description and accompanying drawings.

BEST MODE FOR CARRYING OUT THE INVENTION

Copending, commonly-assigned U.S. patent application Ser. No. 08\386,619 filed on Feb. 10, 1995 is incorporated by reference in its entirety herein.

Referring to FIGS. 1–3A, the suture package 5 of the present invention is illustrated. The suture package 5 is seen to have tray 10 and lid member 70. The tray 10 is seen to have flat base member 20. The flat base member 20 is seen to have top 21, bottom 22, and outer periphery 24. The flat base member 20 is seen to have a generally oval configuration wherein opposed, substantially parallel, longitudinal sides are connected by opposed semi-circular end sections; however, the flat base member may have other configurations including other oval configurations, circular configurations, polygonal configurations, combinations thereof and the like.

Figure 2:
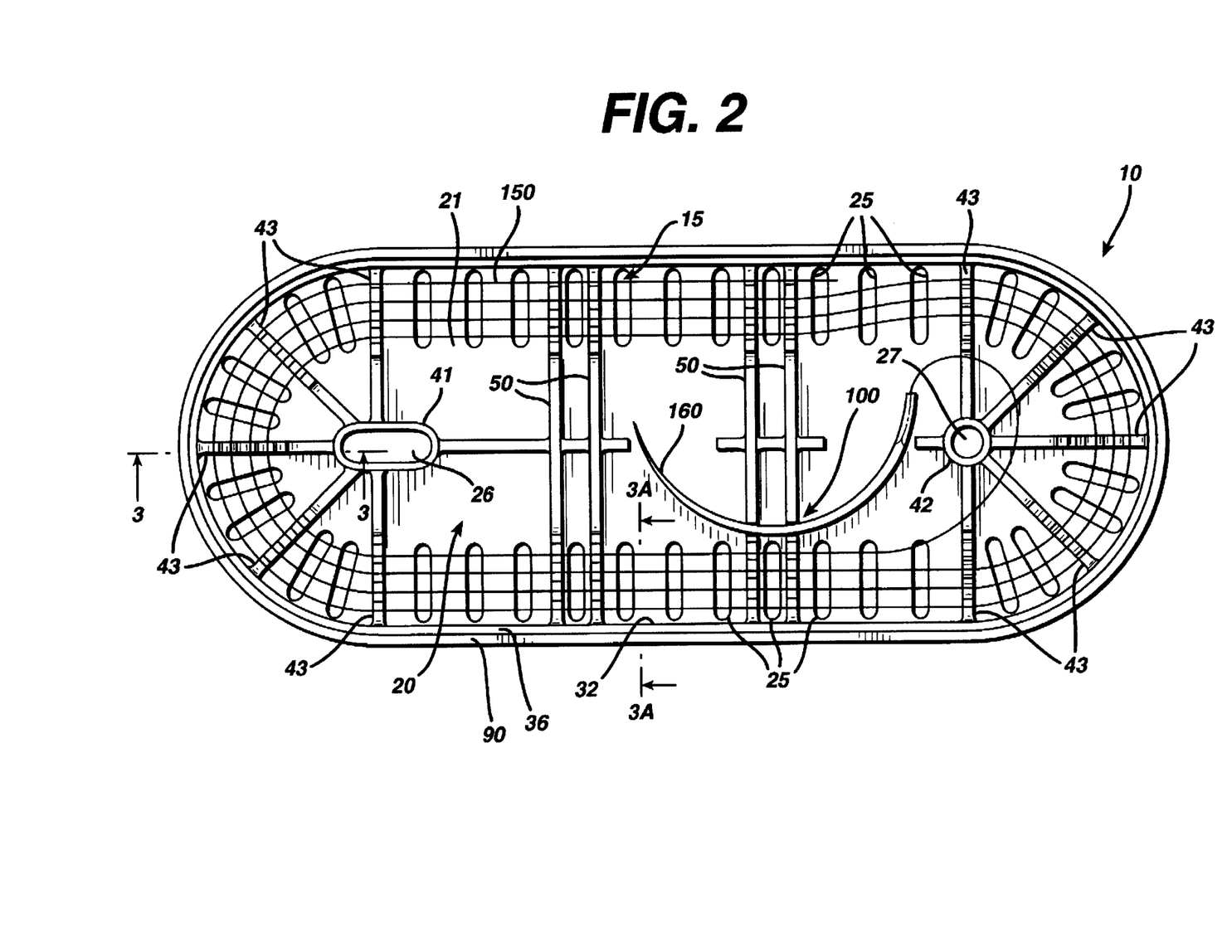
FIG. 2 is a top view of a package of the present invention with the lid member removed illustrating a tray having a suture loaded in the channel and a surgical needle mounted in the needle park; the tray is seen to have a plurality of rib and spoke members containing grooves for retaining a suture.

Also extending from the top 21 of base member 20 are the hub members 41 and 42. The spoke members 43 are seen to extend upwardly from the base member 20 and connect the hub members 41 and 42 with the inner surface 32 of outer wall 30. The spoke members 43 are seen to have tops 44 and sides 45. The spoke members 43 are seen to have grooves 46 separated by ridges 47; the grooves 46 have openings 48 and bottoms 49. The rib members 50 are seen to extend upwardly from the base member 20. The rib members 50 have tops 51 and sides 52. The rib members 50 are seen to have grooves 53 separated by ridges 58. The grooves 53 are further seen to have bottoms 55 and openings 56. The grooves 46 and 53 form a suture winding channel 15. Preferably, the suture channel 15 is formed from a plurality of grooves 46 and 53. The suture channel 15 may have a spiral configuration or may be configured as a plurality of concentric channels. The desired configuration of channel 15 will be accomplished by the layout of the grooves 46 and 53.

Figure 3:
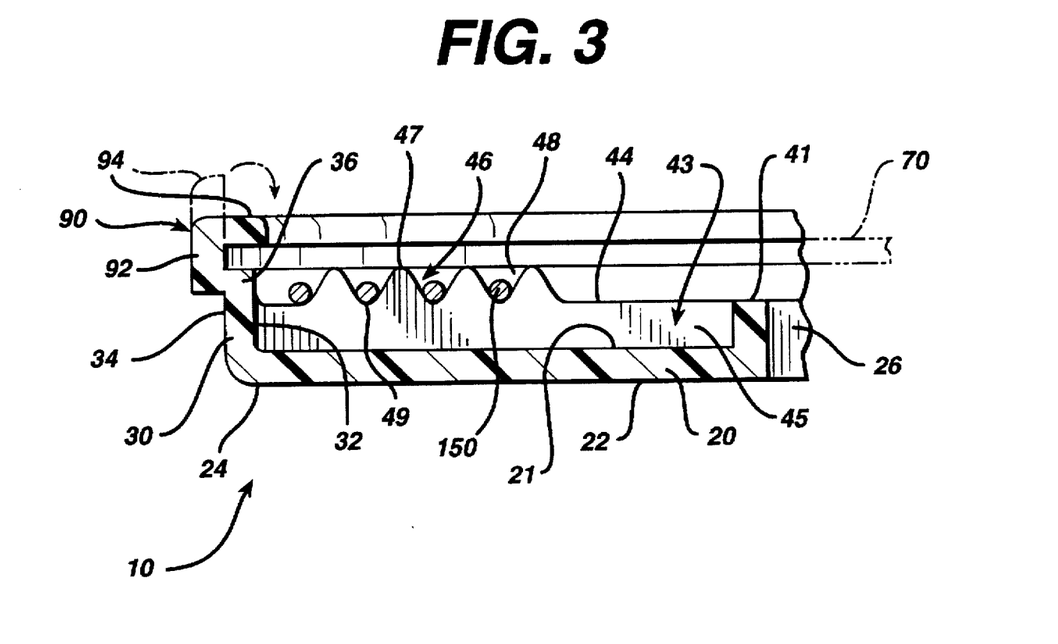
FIG. 3 is a partial cross-section of the package of FIG. 1 taken along View Line 3—3; the lid retention member is seen to be retained in a position on top of the outer wall of the tray.
Figure 3A:
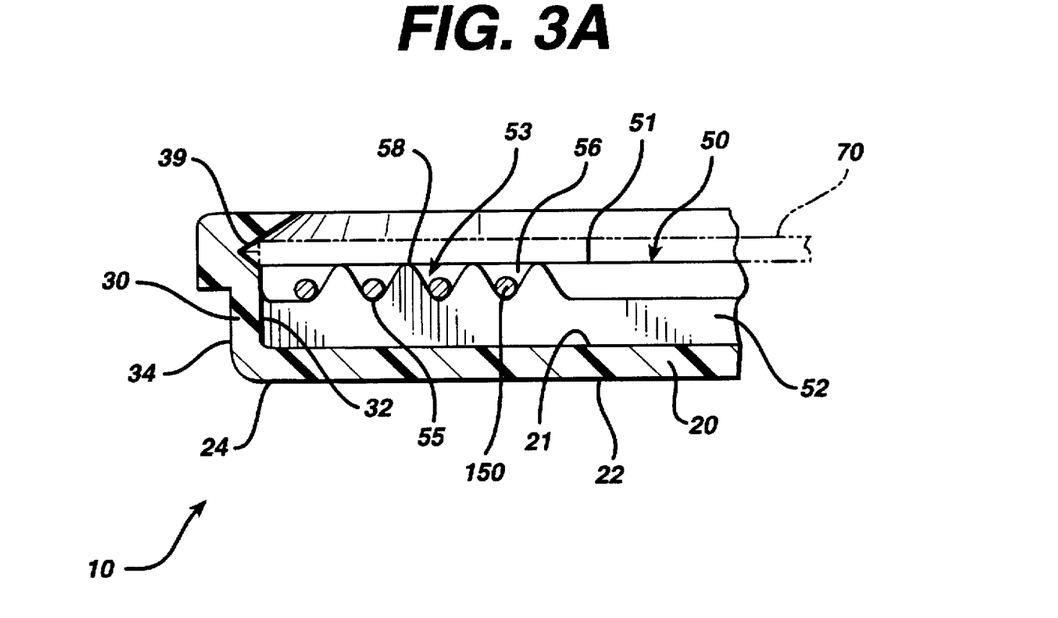
FIG. 3A is a partial cross-sectional view showing an alternate way of retaining the lid member by having a snap groove in the outer wall of the tray.
Figure 10:
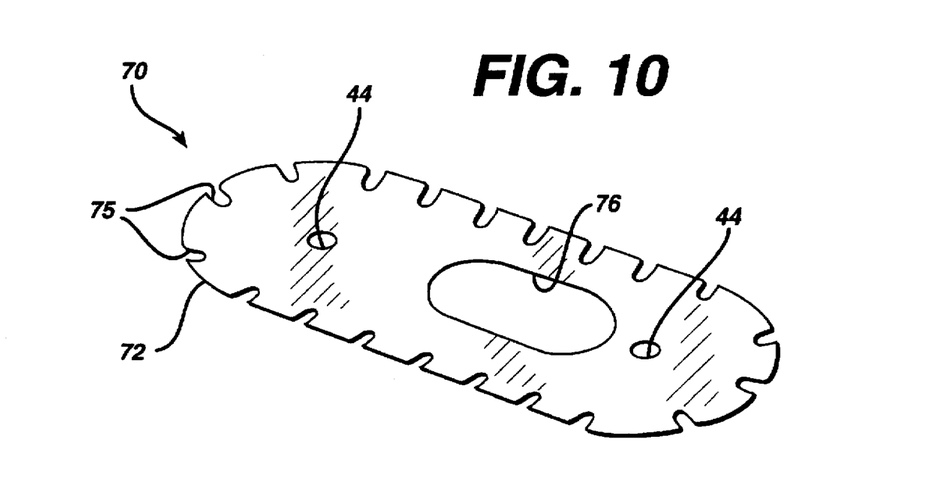
FIG. 10 is a perspective view of a lid member useful in the package of the present invention.

The lid member 70 of the present invention is seen to be a substantially flat member having a configuration which is similar or identical the configuration of the base member 20. The lid member is seen to have periphery 72, winding holes 44, and optional outwardly extending radial openings 75 as seen in FIG. 10. In addition the lid 70 has suture exit opening 76. Exit opening 76 may have any configuration including square, rectangular, oval and the like and combinations thereof however it is particularly preferred that opening 76 have an oval configuration Extending upwardly from the top of the flat base member 20 about the periphery 24 is the outer wall 30. The outer wall 30 is seen to have top 36, inner surface 32, and outer surface 34. Extending from the outer surface 34 near the top 36 of the wall 30 is the closure lip 90. Closure lip 90 is seen to have radially outward extending section 92 and upwardly extending section 94. Closure lip 90 can be bent or deformed inwardly, or staked, in order to secure the lid member 70 to the top 36 of the outer wall 30. Equivalent conventional closure mechanisms can be used to secure lid member 70 to tray 10 including pins extending through the lid member which are heat or ultrasonically fused, cover sleeves, hinged door members, and the like. FIG. 3A illustrates an alternate embodiment of a closure mechanism wherein the outer periphery 72 of lid 70 is retained in a retention groove 39 extending into the inner surface 32 of outer wall 30.

The needle park 100 is seen to be positioned on the top 21 of the base member 20 interior to the grooves 46 and 53 such that a surgical needle 160 mounted in needle park 100 can be withdrawn through exit opening 76 in lid member 70. The needle park 100 preferably is seen to consist of openings 102 in rib members 50. The openings 102 are sufficiently sized to effectively frictionally engage and retain needles 160 mounted therein. The needle park 100 may also consist of conventional needle parks including foam members, flaps, opposed members having deformable edges, and the like and equivalents thereof.

Referring to FIG. 2, the base member 20 is seen to have holes 26 and 27 for receiving conventional mounting pins during the winding process. The base member 20 is also seen to have a plurality of holes 25 in channel 15 for receiving conventional winding pins. The holes 25 also serve as vacuum ports in order to draw a vacuum upon the base member 20 as sutures 150 are being loaded into the suture channel 15.

A surgical needle 160 and suture 150 combination is wound into tray 10 of the present invention in the following manner. The tray 10 is mounted to a winding fixture wherein conventional mounting pins are inserted through mounting holes 26 and 27. In addition, winding pins are inserted through the holes 25 in the channel to guide the suture 150 into the winding channel 15. A surgical needle 160 is mounted in needle park 100. The fixture is then rotated and suture 150 is placed in winding channel 15. At the same time, a vacuum is drawn upon the holes 25 to assist in maintaining the suture 150 in the winding channel 15.

Figure 4:
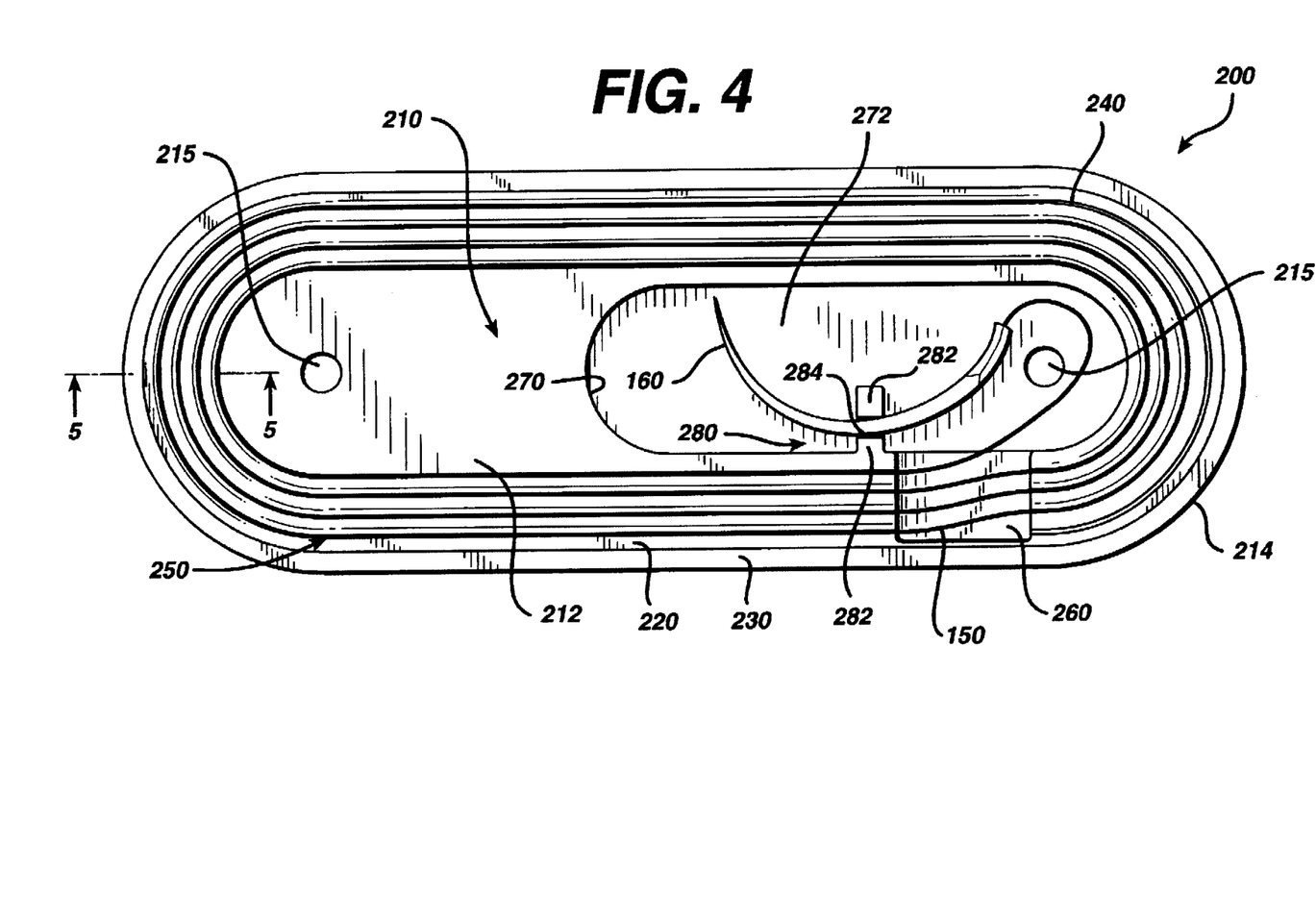
FIG. 4 is a top view of an alternate embodiment of the package of the present invention having concentric suture grooves in the base member.
Figure 5:
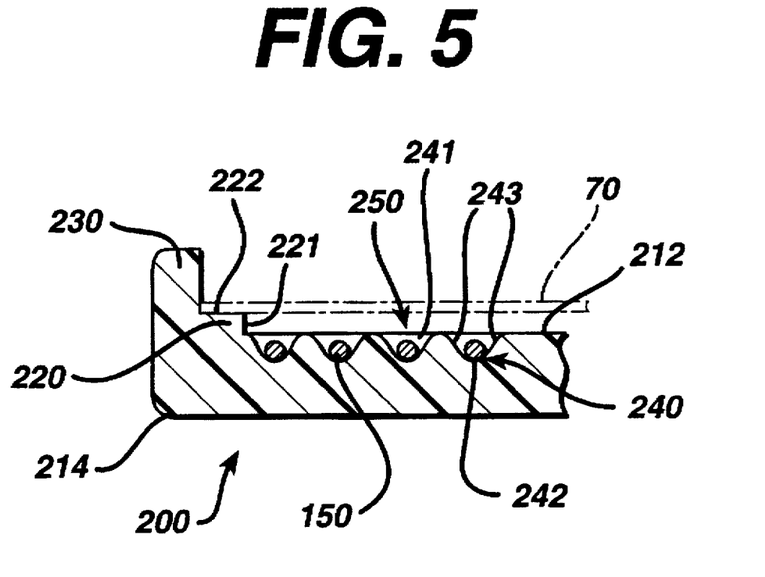
FIG. 5 is a partial cross-sectional view along View-Line 5—5 of the package of FIG. 4 illustrating a lid mounted to the top of the outer wall of the tray.
Figure 6:
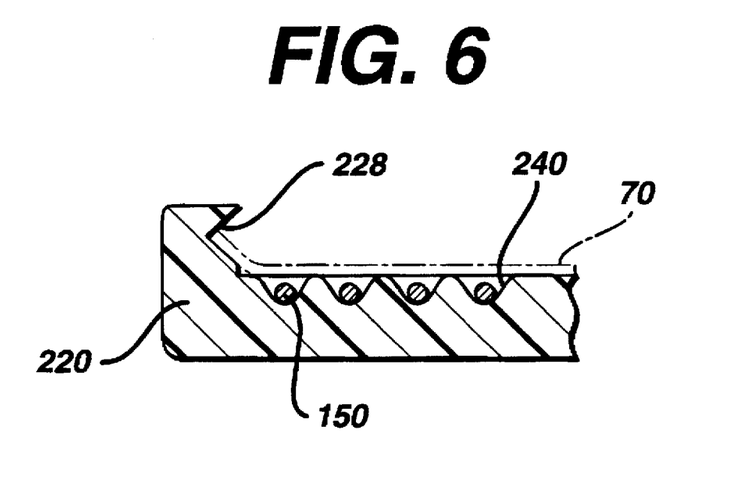
FIG. 6 is a partial cross-sectional view showing an alternate way of retaining the lid by having a snap groove in the outer wall of the tray.

Another embodiment of the package of the present invention is seen in FIGS. 4, 5 and 6. Package 200 is seen to have flat, oval shaped base member 210. Base member 210 may have other configurations including circular, rectangular, square, combinations thereof and the like. Base member 210 is seen to have pin openings 215 therethrough. Base member 210 is also seen to have top 212 and outer periphery 214. Extending upwardly from the top 212 of the periphery 214 of base member 210 is the outer wall 220. Outer wall 220 is seen to have inner surface 221 and top 222. Extending from the top 222 of outer wall 220 is the closure lip 230. Grooves 240 are seen to extend into top 212 of base member 210. The grooves 240 are seen to have top opening 241, bottoms 242 and sides 243. The grooves 240 are seen to be concentric. The grooves 240 are seen to begin and end on either side of the optional crossover indentation 260. The crossover indentation is a cavity extending into the top of the base member 210. The grooves 240 form the suture-winding channel 250. Interior to the grooves is the needle well 270 extending into the top 212 of the base member 210. Well 270 is a cavity having bottom 272 for receiving a surgical needle 160. Extending upwardly from the bottom 272 of the well 270 is the needle park 280. Needle park 280 is seen to consist of a pair of opposed members 282 separated by an opening 284. A surgical needle 160 is frictionally engaged in the opening 284. A lid member 70 is mounted to the top 222 of the outer wall 220 and retained in place by bonding over the closure lip 230 to engage the outer periphery of the lid 70. An alternate embodiment of a closure mechanism for the package 200 is seen in FIG. 6 in a partial cross section. The lid 70 is retained in the package 200 by retention groove 228 in the inner side of the outer wall 220.

Figure 7:
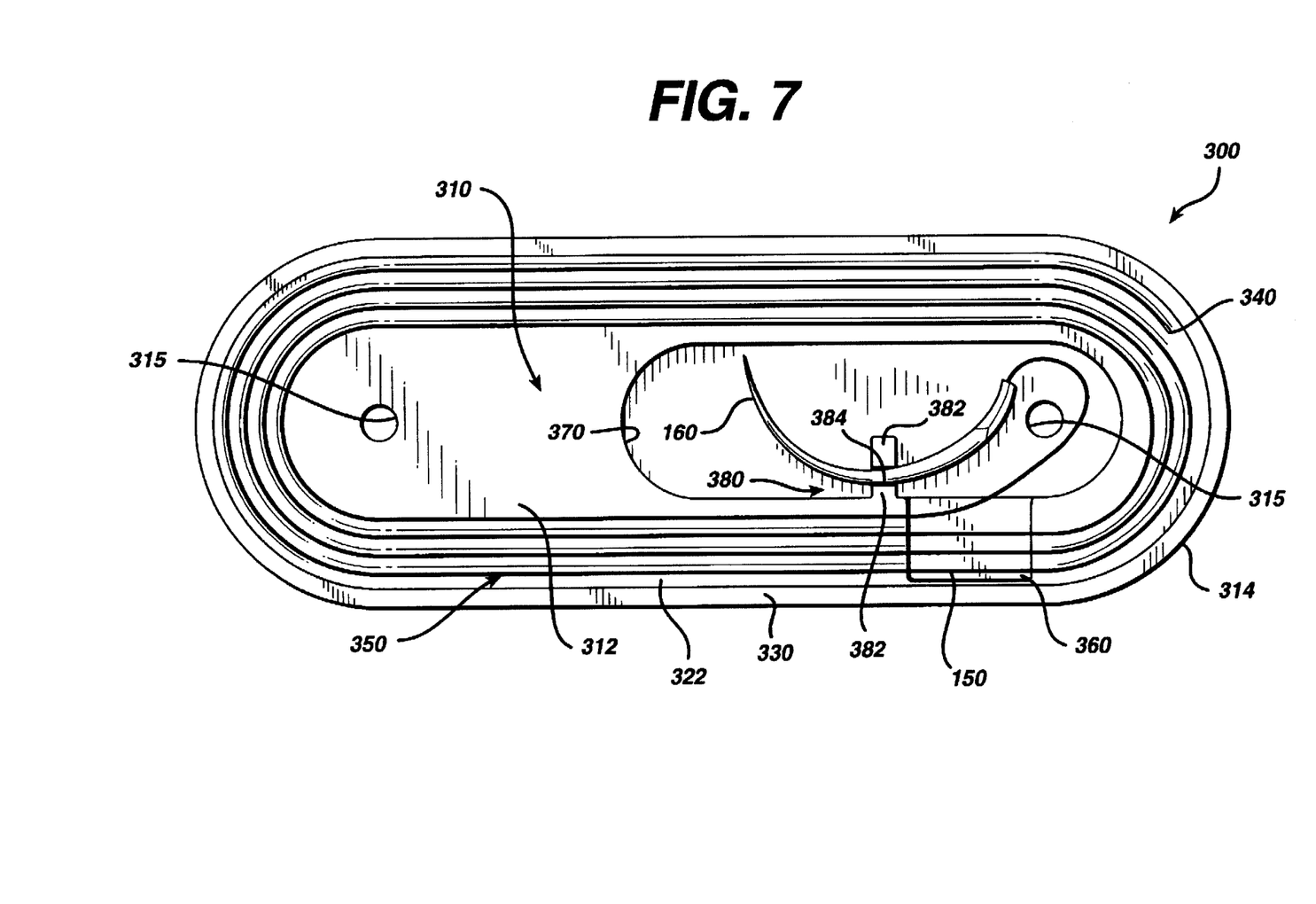
FIG. 7 is a top view of an alternate embodiment of the package of the present invention having a spiral suture groove in the base member.
Figure 8:
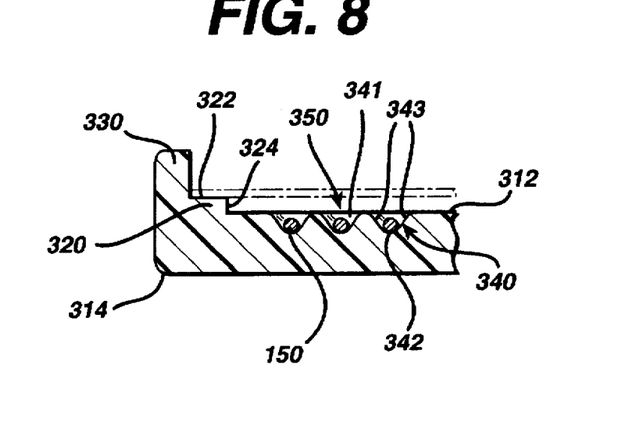
FIG. 8 is a partial cross-sectional view taken along View Line 8—8 illustrating a lid mounted to the top wall of the tray.
Figure 9:
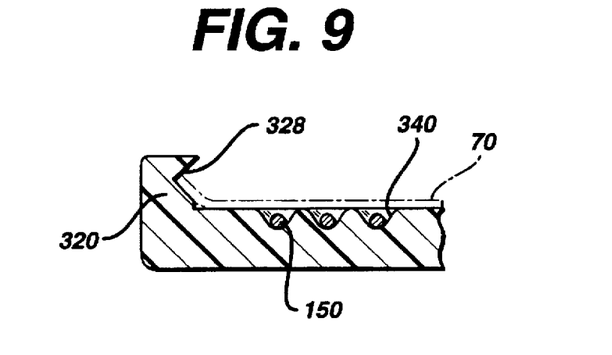
FIG. 9 is a partial cross-sectional view showing an alternate way of retaining a lid by having a snap groove in the outer wall of the tray.

Yet another embodiment of the package of the present invention is seen in FIGS. 7, 8 and 9. The package 300 is seen to have a substantially oval shaped base member 310 having pin openings 315. The base member 310 is seen to have outer periphery 314 and top side 312. Extending from the top side 312 of the outer periphery 314 of base member 210 is the outer wall 320. Outer wall 320 is seen to have top 322 and inner side 324. The closure lip 330 is seen to extend from the top 322 of the outer wall 320. The grooves 340 are seen to extend into the top of 312 of the base member 310 forming a spiral channel 350. The grooves 340 are seen to have openings 341, bottoms 342, and sides 343. The grooves begin and end adjacent to the crossover indentation cavity 360 which extends into the top 312 of base member 310. The needle well 370 is a cavity which extends into the top 312 of the base member 310. The needle well 370 contains the needle park 380 and additionally contains a surgical needle 160 mounted in the needle park 380. The needle park 380 is seen to consist of a pair of opposed members 382 extending from the bottom 372 of the needle well 370. Opposed members 382 are separated by opening 384. A surgical needle is inserted into opening 384 and is frictionally engaged and retained by the opposed member 382. A lid member 70 is mounted to the top 322 of the outer wall 320. The lid 70 is retained in place by bending or staking the closure lips 330 inwardly on top of the periphery of the lid member 70. An alternative lid retention scheme is seen in FIG. 9. Lid 70 is snapped into a retention groove 328 extending into wall 320. Other conventional closure schemes may also be used. The packages 200 and 300 are loaded with sutures using conventional winding apparatuses including winding fixtures and styluses to guide sutures into the grooves.

A surgical needle 160 and suture 150 are withdrawn from the packages of the present invention in the following manner. The needle 160 is grasped by a medical professional with a conventional needle grasper and withdrawn by pulling upward through the lid opening and straight out while the outer periphery of the package is held securely between the index finger and thumb of the medical professional.

It is believed that the suture packages of the present invention may prevent suture "lock-ups" when the sutures are withdrawn from the packages. Although not desiring to be held to any particular theory, one possible explanation is that separating the individual suture winds may prevent entanglements when the suture is subsequently dispensed by allowing each strand to sequentially exit the package between the tops of the ridges or top of the base member and the bottom of the lid, thereby possibly preventing a capstan effect.

The term suture "lock-up" is defined to mean a situation which may occur when attempting to withdraw a suture form a suture package having an oval, circular, or curved winding channel wherein the suture wraps around a core, inner wall, pin, etc., thereby preventing suture withdrawal. Although not desiring to be held to any particular theory, it is believed that "lock-up" may be caused by a capstan effect.

As previously mentioned, the lids of the packages of the present invention are mounted to the trays such that the bottom of a lid is contacting either the tops of ridges or tops of the base members (depending upon the package embodiment), or is in sufficient proximity thereto, to effectively prevent suture strands (i.e., segments) from escaping from the grooves during sterilization, shipping, handling and storage, etc. The suture strands are thusly maintained in a singulated configuration. The lids are constructed and mounted in order to be capable of sufficient upward deflection or displacement to effectively allow sutures and\or suture strands to pass between the tops of ridges, or the top of the base member, and the bottoms of the lids and thereby exit the grooves when sutures are being withdrawn from the packages of the present invention.

The trays of the present invention may be constructed of conventional materials including medical grade cardboard or polymers or combinations thereof.

The trays are typically manufactured from polymers using conventional processes including injection molding, vacuum forming, numerically controlled machining, and standard machining techniques.

The lid members 70 of the present invention may be constructed of conventional medical grade materials such as cardboard or plastic. The lid members 70 are preferably manufactured using conventional manufacturing processes including die cutting and forming.

The surgical needles 160 which can be mounted in the packages of the present invention include any conventional surgical needles including tapered point and cutting point needles. The needles 160 may have curved, semi-curved, straight configurations, and other conventional configurations. The sutures 150 which may be packaged in the packages of the present invention include any of the conventional sutures, absorbable and non-absorbable, such as silk, polypropylene, polydioxanone, and the like and equivalents thereof. The sutures may be braided, woven or monofilament.

Figure 1:
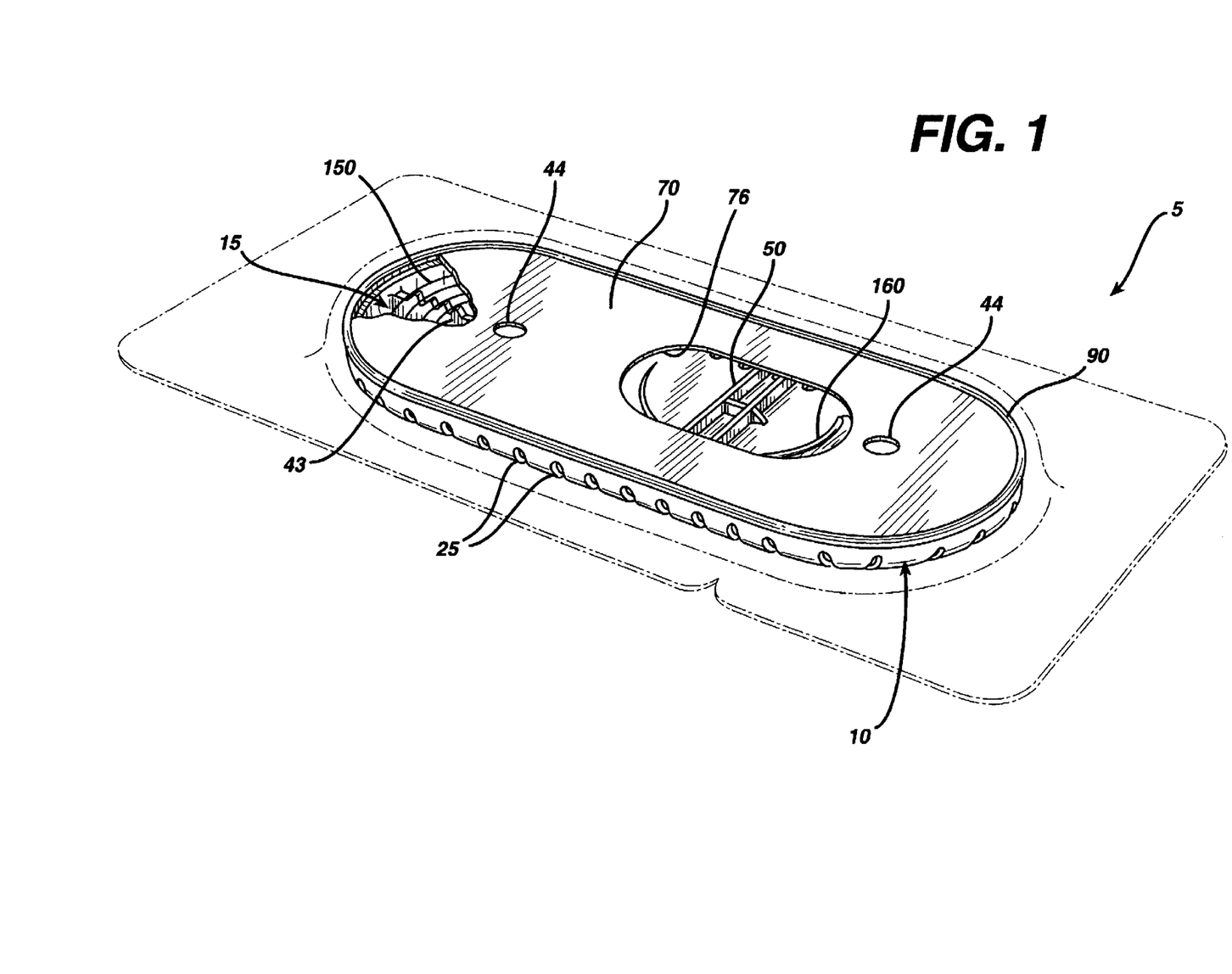
FIG. 1 is a perspective view of a preferred embodiment of a package of the present invention; an outer overwrap package is drawn in phantom.

The suture packages of the present invention are typically packaged in an outer package, such as outer foil package 200 as seen in FIG. 1, to maintain the sterility of the package 5 and its contents. The outer package 200 may be any conventional outer package including foil packages, polymer film, paper, laminates, combinations thereof, and the like. The packages of the present invention are sterilized using conventional sterilization processes including ethylene oxide, radiation, heat, and the like. The packages of the present invention containing needles 160 and sutures 150 may be sterilized prior to or after packaging in an outer package, depending on the type of outer package used and further depending upon the type of sterilization process utilized.

The suture packages of the present invention will preferably contain one suture and one surgical needle, i.e., a single-armed suture. However, it will be appreciated by those skilled in this art that the packages my accommodate double armed-sutures as well as unarmed sutures and multiple sutures and needles.

The suture packages of the present invention have many advantages. The packages can dispense a broad range of suture types and lengths. The packages are adapted to be used on automatic suture loading apparatuses. In addition, the packages of the present invention may reduce the incidence of suture "lock-ups". Furthermore, the grooves maintain sutures in a preferred singulated "arranged wind" pattern during shipping and handling while allowing easy withdrawal.

Although this invention has been shown and described with respect to detailed embodiments thereof, it will be understood by those skilled in the art that various changes and forming detail may be made without departing from the spirit and scope of the claimed invention.

We claim:

1. A suture package, comprising:
   a substantially flat base member having a top side, a bottom side, and an outer periphery;
   an outer wall extending upwardly from the top side of the base member about the periphery of the base member, said outer wall having a top, an outer surface, and an inner surface;
   at least one groove in the base member for receiving a suture, each said groove having an opening in the top side of the base member, a bottom and sides;
   a needle park means for receiving a needle, said needle park means centrally mounted to the top side of the base member within the interior wall; and,
   a flat, lid member having a top, a bottom, a suture discharge opening, and an outer periphery, wherein the lid member is mounted on the top of the outer wall; and,
   means for securing the lid member to the top of the outer wall.

2. The package of claim 1 additionally comprising a surgical needle and suture.

3. The package of claim 2, wherein said package and needle and suture are sterile.

4. The package of claim 3 further comprising a sealed outer package.

5. The package of claim 4 wherein the lid member additionally comprises a plurality of radial slots extending into the periphery.

6. The package of claim 1 wherein plural said grooves comprise a spiral channel.

7. A suture package, comprising:
   a substantially flat base member having a top side, a bottom side, and an outer periphery;
   an outer wall extending upwardly from the top side of the base member about the periphery of the base member, said outer wall having a top, an outer surface, and an inner surface;
   at least one groove in the base member for receiving a suture, each said groove having an opening in the top side of the base member, a bottom and sides; and,
   a needle park means for receiving a needle, said needle park means centrally mounted to the top side of the base member within the interior wall; and,
   means for securing a lid member to the top of the outer wall.

8. The package of claim 7 additionally comprising a surgical needle and suture.

9. The package of claim 8, wherein said package and needle and suture are sterile.

10. The package of claim 9 further comprising a sealed outer package.

11. The package of claim 7 wherein plural said grooves comprise a spiral channel.

* * * * *